United States Patent
Gross

(10) Patent No.: US 6,312,409 B1
(45) Date of Patent: Nov. 6, 2001

(54) DEVICE FOR GENERATING A PULSATILE FLUID DRUG FLOW

(75) Inventor: Joseph Gross, Moshav Mazor (IL)

(73) Assignee: Elan Corporation, PLC, Athlone (IE)

( * ) Notice: Subject to any disclaimer, the term of this patent is extended or adjusted under 35 U.S.C. 154(b) by 0 days.

(21) Appl. No.: 09/331,648

(22) PCT Filed: Dec. 30, 1997

(86) PCT No.: PCT/IE97/00090

§ 371 Date: Sep. 7, 1999

§ 102(e) Date: Sep. 7, 1999

(87) PCT Pub. No.: WO98/29662

PCT Pub. Date: Jul. 9, 1998

(30) Foreign Application Priority Data

Dec. 31, 1996 (IR) ....................................... 960927

(51) Int. Cl.$^7$ .......................... A61M 37/00; A61M 5/00
(52) U.S. Cl. .......................... 604/131; 604/247; 604/256
(58) Field of Search .............................. 604/131, 132, 604/134, 167.01–167.03, 246, 247, 249, 256; 601/148–150; 251/282, 331; 137/535

(56) References Cited

U.S. PATENT DOCUMENTS 3,414,186 * 12/1968 Jorgensen et al. .
4,350,477 * 9/1982 Mazal .
5,281,108 * 1/1994 Brooke .

* cited by examiner

Primary Examiner—Richard K. Seidel
Assistant Examiner—Michael Hayes
(74) Attorney, Agent, or Firm—Kathleen Maher Lynch

(57) ABSTRACT

A device (10) for generating a pulsatile fluid drug flow comprises a housing (11) containing an expandable-contractible chamber (12) having an inlet (14) and an outlet (15), a valve (16) associated with the outlet (15) which is actuated by the expansion and contraction of the chamber (12), and means (13, 23) for biasing the chamber (12) to its contracted state. When the inlet (14) is connected to a pressurised fluid drug supply the chamber (12) is expanded by the drug, and this expansion of the chamber (12) actuates the valve (16) to open, thereby allowing release of the drug from the chamber (12), following which the chamber (12) contracts under the influence of the biasing means (13, 23), this contraction in turn actuating the valve (16) to close thereby allowing the chamber (12) to refill. By this mechanism, a constant supply of liquid, such as from an osmotic or elastomeric drug delivery pump, can be converted to a pulsatile flow, which may provide a more suitable delivery of certain drugs.

7 Claims, 6 Drawing Sheets

DEVICE FOR GENERATING A PULSATILE FLUID DRUG FLOW

TECHNICAL FIELD

This invention relates to drug delivery devices and in particular to pulsatile drug delivery devices.

BACKGROUND ART

Pumps for delivering drugs to a human or animal subject range from simple cheap devices to expensive, complicated microchip-controlled devices. Amongst the cheapest and least complicated devices are osmotic and elastomeric pumps.

Osmotic pumps such as the "ALZET" (Trade Mark) pump produced by the Alza Corporation, Calif., rely on osmotic pressure developed between an aqueous environment and an osmotic solution to drive a drug from a reservoir. Elastomeric pumps such as the "INFUSOR" (Trade Mark) pump produced by Baxter Healthcare Corporation, Ill., rely on the contraction of an expanded elastomeric reservoir to drive the drug from the reservoir. Both types of pump are advantageous primarily as a result of their simplicity, cheapness and reliability. Developments in technology have led to a situation where a highly reliable rate of drug delivery can be obtained from such devices.

Similar simple devices include pumps where the contraction of the reservoir is driven by a spring, by the generation of gas in a simple electrolytic cell, or the generation of gas by a chemical reaction. Again, cheap devices having a reliable delivery rate are available using such technologies, although even in devices employing an electrolytic cell the expense and complexity is increased by the necessity of including a battery.

The primary limitation with such devices, some of which have been available since the 1970s, is that they are only suitable in situations where a steady, continuous flow of drug is desired. This immediately precludes their use where a variation in the drug flow rate is required. One particular example of such a case is if a pulsatile drug flow is desired. This method of delivering drugs has become important in recent years. A good overview of the types of situations where a pulsatile drug flow is advantageous can be found in "Pulsatile Drug Delivery—current applications and future trends" ed. Gurny, Junginger and Peppas (published by Wissenschaftliche Verlagsgesellschaft mbH, Stuttgart, 1993). One of the main reasons why pulsatile drug delivery may be advantageous is that a constant supply of drug does not always give rise to constant effects. Furthermore, the body may respond better, in the case of some drugs, to a pulsatile delivery regime.

While other devices have certainly been disclosed which can be used to effect pulsatile drug delivery, such devices in no way approach the simplicity or cheapness of the basic single rate devices referred to above. For example, the devices may rely on microprocessors or electronic timing circuits to switch delivery on and off, or they may employ continuous gas generation which is relieved periodically by a valve which snaps open to effect a periodic cyclical generation of driving pressure. These devices employ mechanisms which are in many cases less reliable than single rate devices, and they are generally significantly more expensive to produce.

The present invention seeks to overcome these disadvantages and to provide pulsatile delivery devices which are simple, cheap and can employ the existing technology which has proved successful in relation to single rate drug pumps.

DISCLOSURE OF INVENTION

Thus, the invention provides a device for generating a pulsatile fluid drug flow, comprising a housing containing an expandable-contractible chamber having an inlet and an outlet, a valve associated with the outlet which is actuated by the expansion and contraction of the chamber, and means for biasing the chamber to its contracted state, such that when the inlet is connected to a pressurised fluid drug supply the chamber is expanded by the drug, the expansion of the chamber actuating the valve to open, thereby allowing release of the drug from the chamber and enabling the contraction of the chamber under the influence of the biasing means, this contraction in turn actuating the valve to close thereby allowing the chamber to refill.

As used herein, the term, "liquid drug", is meant to encompass any drug-containing fluid capable of being passed through the hollow needle in a controlled manner, such as a liquid, solution, gel or fine suspension. There is essentially no limitation on the type of liquid drug which can be used with the invention other than to exclude those liquid drugs which would be inappropriate to deliver to the subject intravenously, intradermally or subcutaneously. Representative drugs include peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and anti-diuretic agents.

Typical drugs include peptides, proteins or hormones such as insulin, calcitonin, calcitonin gene regulating protein, atrial natriuretic protein, colony stimulating factor, betaseron, erythropoietin (EPO), interferons such as $\alpha$, $\beta$ or $\gamma$ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphafiol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof.

Other drugs include antiulcer agents, such as but not limited to cimetidine, and ranitidine; antibiotics; anticonvulsants; antiinflammatories; antifungals; antipsychotics; corticosteriods; immunosuppressants; electrolytes; nutritional agents and vitamins; general anesthetics; antianxiety agents, such as but not limited to compazine; and diagnostic agents.

The device according to the invention automatically generates pulses of a drug from any pressurised supply. It converts any pressurised supply into a pulsatile flow without the need for any power source and can therefore be designed as an extremely simple unpowered mechanical device. It will be appreciated that the device according to the invention can be coupled to a standard continuous drug pump and can therefore provide a simple, cheap and effective pulsatile drug source which has none of the complexity of existing variable rate powered drug pumps.

The frequency of pulsation and the volume of the pulses can be selected by the design of the device. Particular consideration can be given to the sizes of the chamber, inlet and outlet, the strength of the biasing means, the pressure and volume provided by the drug supply, the nature of the valve, and the nature of the coupling between the valve and the expansion and contraction of the chamber.

Suitably, the valve is a bistable valve which is actuated between opened and closed states.

A bistable valve is preferred because it has a tendency to remain either open or closed (in which positions the device performs most predictably), and spends very little time between the open and closed positions.

Preferably, the valve remains closed as the chamber expands and the valve remains open as the chamber contracts.

This provides the most efficient pumping for a given chamber volume as the chamber refills and empties substantially completely during each pumping cycle.

Suitably, the means for biasing the chamber to its contracted state comprises a resilient member.

This resilient member preferably is a spring, an elastic membrane or some other elastic material which can be continually stressed and which continues to exert its biasing effect.

In certain embodiments, suitably, the resilient member acts on a displaceable member which at least partially bounds the chamber such that the expansion and contraction of the chamber occurs by the displacement of said displaceable member.

In certain other embodiments, suitably, the resilient member comprises a displaceable member which at least partially bounds the chamber such that the expansion and contraction of the chamber occurs by the displacement of said displaceable member.

In either case, the displaceable member enables the chamber to expand and to contract. Thus it can be in the form of a movable wall section, a diaphragm, a membrane or a bellows, for example.

In a preferred embodiment, the expansion and contraction of the chamber is controlled by the displacement of a displaceable member, and the displacement of said displaceable member also controls the actuation of said valve.

Suitably, the actuation of said valve exhibits a hysteresis effect with respect to the expansion and contraction of the chamber.

In other words, the valve does not begin to open immediately when the chamber starts to expand, but instead it lags behind to the extent that the chamber is able to fill up before the valve opens. Similarly the closing of the valve is not actuated until the chamber has emptied.

Preferably, the valve is actuated by the action of a bistable actuating member linked to the displaceable member.

Thus, the actuating member is triggered from one state to another state by the movement of the displaceable member, and this change in the bistable member is in turn transmitted to the valve.

In a preferred embodiment, the bistable actuating member is in the form of a resilient curved member which can be flipped between convex and concave configurations.

A suitable such member is a thin convex metal disc or metal strip which can be inverted to a concave configuration.

Suitably, the bistable actuating member acts on a component of the valve to open and close the valve as the actuating member moves between its bistable configurations.

The nature of said component and the interaction between the actuating member depends entirely on the type of valve employed and the type of actuating member used. In an illustrated arrangement, however, said component of the valve is shaped to allow the bistable actuating member to undergo an initial deformation or movement without actuating the valve, such that the actuation of the valve only occurs when the actuating member undergoes the full transition between its bistable configurations.

Furthermore, in that arrangement, said component of the valve is in the form of a longitudinally extending element having a section of lesser thickness intermediate two sections of greater thickness, and the bistable actuating member is provided with an aperture which moves freely with respect to the section of lesser thickness but which engages the sections of greater thickness.

In one embodiment, the outlet is formed by an aperture in the displaceable member, said aperture forming a seat for the valve, and the valve comprises a blocking member which is adapted to move into and out of sealing engagement with the seat, thereby opening and closing said outlet. This arrangement positively links the opening and closing of the valve with the movement of the displaceable member, further ensuring that the chamber empties and refills correctly.

Additionally, the blocking member is carried on a second displaceable member and the aperture communicates with the exterior of the device via a gap between the displaceable members. Preferably, the second displaceable member is elastic and is biased to a position in which the blocking member is in sealing engagement with the aperture.

The shape of the valve component and the actuating member thus allow for the hysteresis effect referred to above, as the actuating member is able to begin changing configurations without influencing the valve; the valve is only actuated when the actuating member has fully changed configurations, i.e. it has moved from a position where it was engaging one of said sections of greater thickness to a position where it engages the other section of greater thickness, and the intermediate section allows the actuating member to make this transition before the valve is actuated.

Preferably, the device is adapted to be connected to and to receive a supply of fluid drug from a continuous flow drug pump.

Such a drug pump need not necessarily provide an unvarying flow rate, and while there can be interruptions in the flow from the drug pump, the pump will essentially act as a substantially continuous supply for the device.

More preferably, the device is adapted to be connected to and to receive a supply of fluid drug from a drug pump selected from an osmotic pump, an elastomeric pump, a spring driven pump and a gas driven pump.

Thus, the device can be connected to a simple, cheap pump in order to adapt the pump for pulsatile delivery.

Suitably, the device further comprises means for delivering the drug from the outlet to a subject. This can be in the form of a tube extending from the outlet having a needle mounted on the end thereof distal from the outlet. This arrangement is useful for intravenous, subcutaneous or intradermal delivery of the drug.

The invention further provides a pulsatile drug delivery system comprising a device according to the invention and a continuous flow drug pump.

Suitably, the pump provides a continuous basal flow to a subject which is supplemented by a bolus pulsatile flow from the device.

Thus, the pump both delivers drug continuously to the subject and continuously fills the device; when the chamber of the device is filled the valve opens to provide a bolus pulse of the drug to the subject.

BRIEF DESCRIPTION OF DRAWINGS

The invention will be further illustrated by the following description of embodiments thereof, given by way of example only with reference to the accompanying drawings, in which.

MODES FOR CARRYING OUT THE INVENTION

Figure 1:
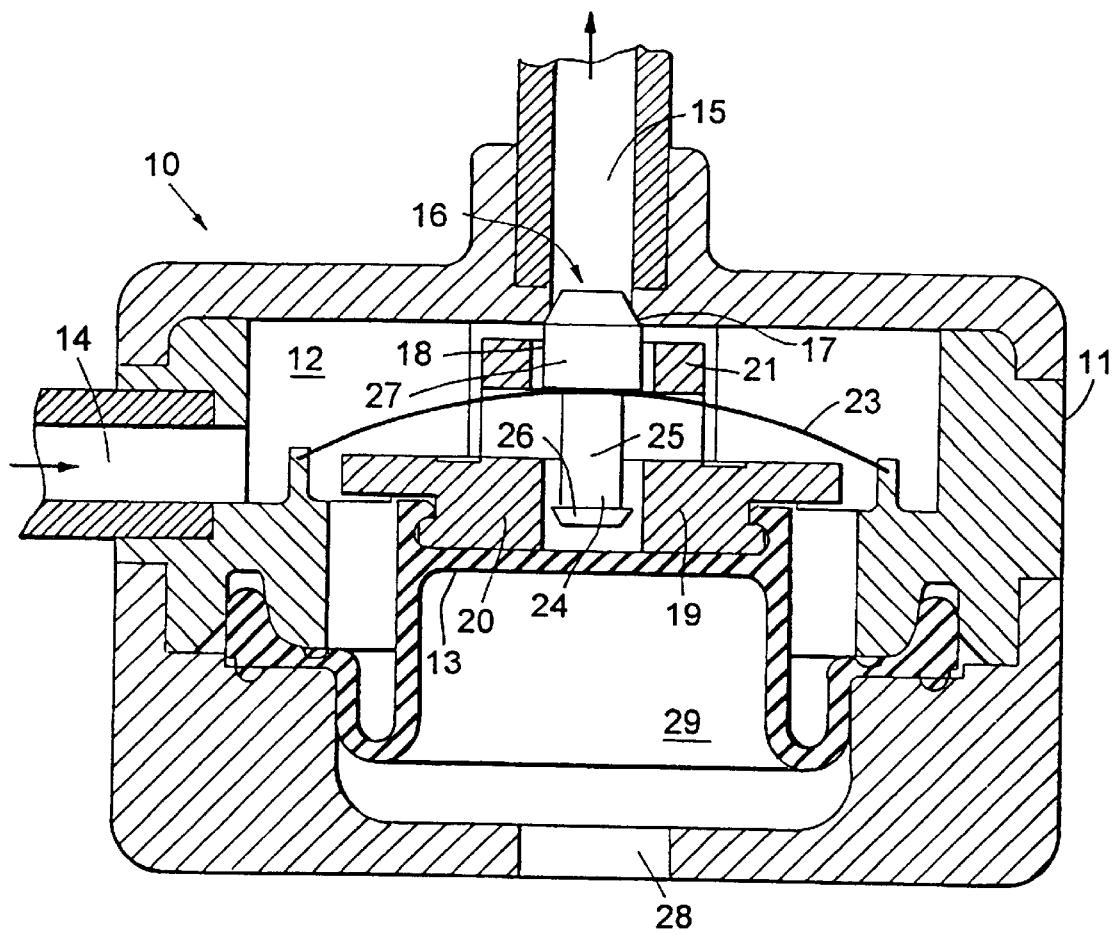
FIG. 1 is a sectional elevation of a device according to the invention.

In FIG. 1 there is indicated, generally at 10, a device according to the invention comprising a generally cylindrical housing 11, seen here in sectional elevation, which contains an internal chamber 12 defined in part by a diaphragm 13. Diaphragm 13 is able to move downwards and upwards so as to expand and contract chamber 12. Chamber 12 is provided with an inlet 14 which can be connected to a continuous drug pump and an outlet 15 through which drug can be pumped from the chamber 12. A valve 16, in the form of a valve seat 17 and a blocking member 18, controls the flow of drug from chamber 12 through outlet 15.

Diaphragm 13 is provide with support member 19 which comprises a lower annular section 20 and an upper annular section 21. An actuating member in the form of a spring 23 is mounted within housing 11 such that it is situated between the upper and lower annular sections 20,21. Spring 23 consists of a thin convex circular metal disc which can be flipped to a concave configuration as a result of sufficient downward motion from upper annular section 21 and which can then be flipped back to the convex configuration (shown) as a result of sufficient upward motion from lower annular section 21.

Blocking member 18 is provided with a stem 24 which defines a section of lesser thickness 25 intermediate two sections of greater thickness defined by abutments 26,27, and the spring 23 is provided with an aperture(not visible) which moves freely with respect to the section of lesser thickness 25 but which abuts against the abutments 26, 27, such that the conversion of the spring 23 between its convex and concave configurations results in an accompanying downward or upward motion of member 18.

As the spring 23 is essentially a bistable mechanism, the valve 16 can only rest in an open position (in which the spring 23 is concave and the blocking member 18 is pulled down, away from valve seat 17) or a closed position as shown in FIG. 1 (in which the spring 23 is convex and the blocking member 18 is pushed up, in sealing contact with valve seat 17).

The housing 11 is provided with an aperture 28 which ensures that the space 29 below diaphragm 13 remains at atmospheric pressure. This ensures that the diaphragm is free to move downwards as the pressure increases in the chamber 12.

Diaphragm 13, although free to move upwards and downwards, is formed of a resilient elastomeric material and is biased to return to the upward position shown in FIG. 1. Thus, if downward pressure is exerted on (as when the chamber 12 fills with drug from a continuous supply) it moves down to expand the chamber 12. If, however, the downward pressure is removed, diaphragm 13 has a tendency to restore its original shape, i.e. to contract the chamber 12.

FIG. 1 shows the device 10 as it would appear at the beginning of a pumping cycle. The device 10 receives a constant flow of fluid through inlet 14 and this gradually pushes diaphragm 13 down as the pressure in the chamber 12 increases with the incoming fluid. As diaphragm 13 moves down and pulls support member 19 with it, pressure is exerted on spring 23 which resists but nevertheless deforms under the pressure. When the chamber 12 is almost full the spring 23 reaches the transition point at which it inverts to a concave configuration. This conversion is almost instantaneous and the transition is illustrated in FIG. 2.

Figure 2:
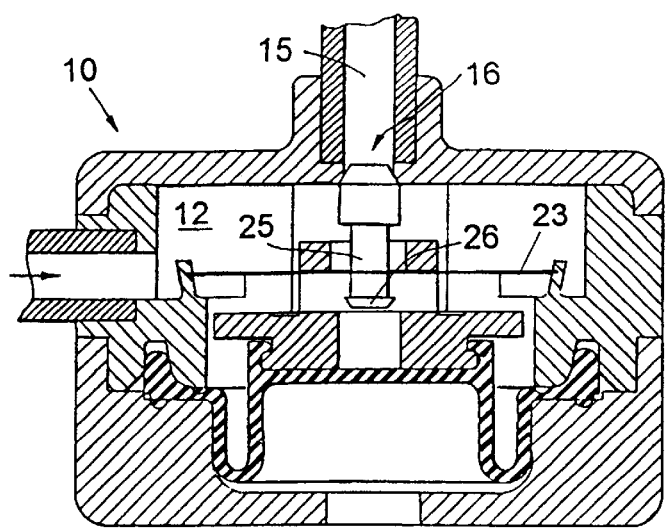
FIGS. 2–4 show the device of FIG. 1 as it progresses through a pumping cycle.

At the point in the cycle shown in FIG. 2, the chamber 12 is essentially full and the spring 23 is flipping downwards, but the valve 16 remains closed due to the pressure differential between the chamber 12 and the outlet 15. Because spring 23 is free to move with respect to the section of lesser thickness 25, the valve 16 is only influenced by the spring 23 when it strikes the lower abutment 26. This point is illustrated in FIG. 3.

Figure 3:
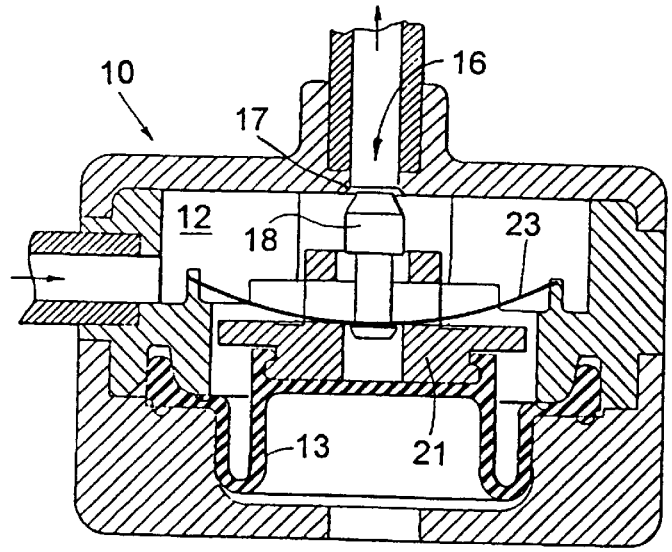

In FIG. 3, the valve 16 has been opened by the action of spring 23 on blocking member 18. the liquid drug within chamber 12 (under pressure with respect to the outlet) is therefore free to escape through the outlet 15 via the gap defined between blocking member 18 and valve seat 17.

The escape of liquid and the release of pressure allows diaphragm 13 to move upwards and thereby contract chamber 12. As indicated above, diaphragm 13 is biased to move back to its original shape and this assists in emptying the chamber 12. as it begins to move back up lower annular section 21 pushes spring 23 (but not blocking member 18) upwards, causing it to distort and flip back to the convex configuration. The transition is shown in FIG. 4.

Figure 4:
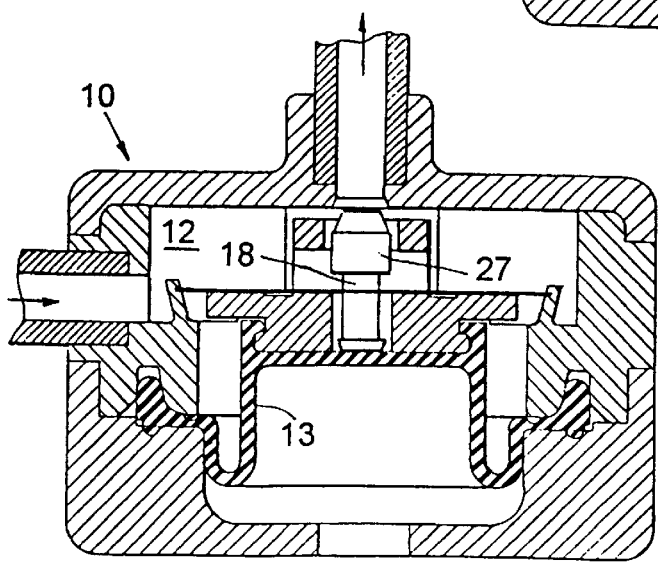

Referring to FIG. 4, it can be seen that diaphragm 13 has returned to the upward position, thereby emptying the chamber of excess drug (although chamber 12 never actually empties in use and is always filled with drug, the volume of the chamber expands to "fill the chamber" and contracts to "empty the chamber").

The preferred volume of chamber 12 ranges from 0.1 to 10.0 millilitres. The preferred flow rate ranges from 0.04 to 10 ml/hr. However, it will be understood that the chamber volume, flow rate and number of pulse cycles per unit time will all vary with the subject and the type of fluid in the chamber.

It is important to note that the configuration of device 10 in FIG. 4 is not identical to the configuration in FIG. 2, although they look similar: in FIG. 2 the chamber 12 is almost full but the valve 16 is still closed and remains closed until the spring 23 completes the transition to the concave position, while in FIG. 4 the chamber 12 is almost empty but the valve 16 is still open and remains open until the spring 23 completes the transition to the convex position at which point it will engage the upper abutment 27 to close the valve. If necessary the blocking member 18 can be mounted on a guide which imparts a slight degree of friction to the upward/downward movement of the blocking member 18, in order to ensure that the valve 16 does not open or close prematurely as a result of a shock or vibration.

When the transition illustrated in FIG. 4 is completed the device returns to the configuration of FIG. 1 and the pumping cycle begins again. In practice the device receives the drug through the inlet 14 at a slow rate so that the time taken to fill the device (i.e. making the transition from FIG. 1 to FIG. 2) determines the period of the cycle. Once the spring 23 reaches the transition point shown in FIG. 2, the remainder of the cycle occurs extremely quickly by comparison. As an example, the inflow rate of the drug could be set to fill the chamber 12 in 1 hour. The actual length of the pulse (between the opening and closing of the valve) might be less than 1 second.

Figure 5:
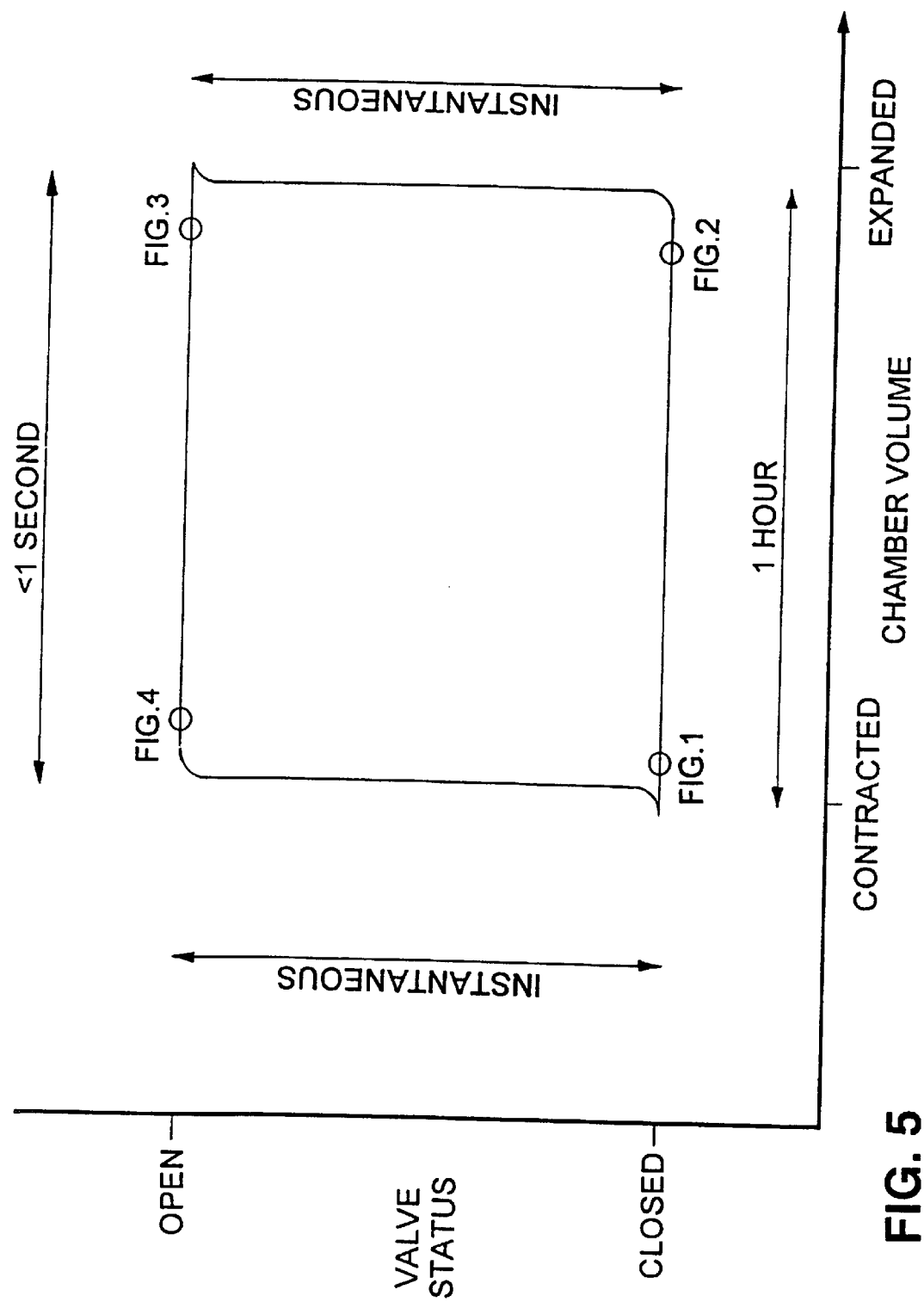
FIG. 5 is a graphical representation of the pumping cycle.

In FIG. 5, there is a graphical representation of the pumping cycle in terms of the volume of the chamber 12 and the status of the valve 16. From this one can see what is meant by a hysteresis effect as the cycle can be described in terms of a hysteresis loop. In FIG. 5, the points during the cycle which are depicted in FIGS. 1–4 are indicated. An indication of the timescale is also provided.

Figure 6:
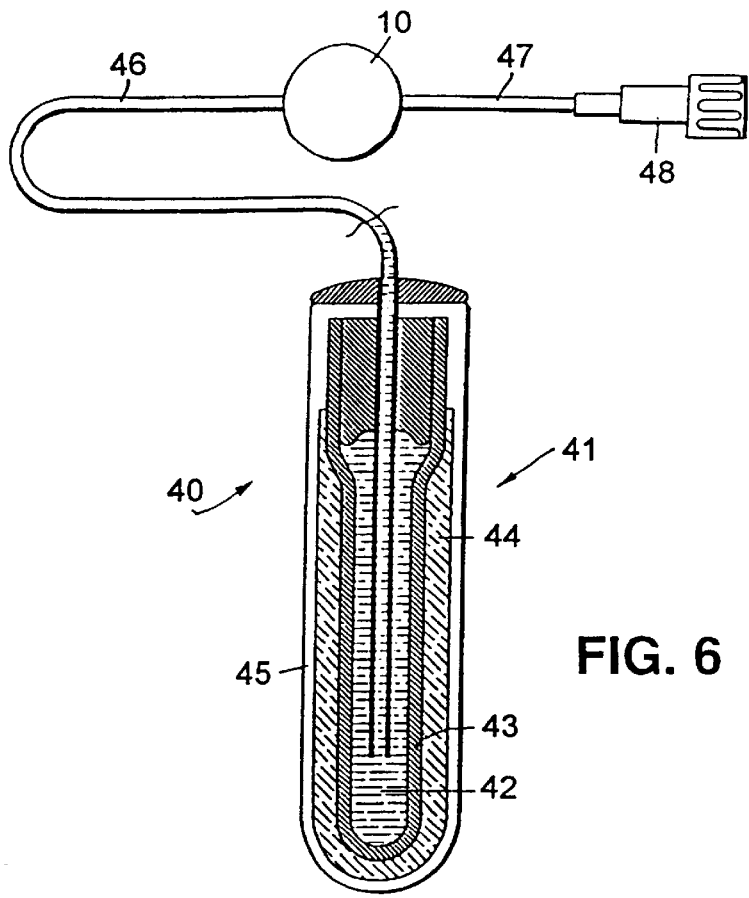
FIG. 6 shows a system according to the invention incorporating an osmotic pump.

In FIG. 6 there is indicated, generally at 40, a system according to the invention comprising a device 10 as previously described and an osmotic pump, indicated generally at 41 in sectional elevation.

Pump 41 is of a type well known to the skilled person; it comprises a drug reservoir 42 defined by a flexible impermeable wall 43, a saturated solution of an osmotic agent 44 surrounding the reservoir 42 and bounded by a semipermeable wall 45 which permits the passage of solvent molecules but prohibits the passage of solute molecules such that when placed in an aqueous environment an osmotic pressure develops across wall 45 which serves to compress the reservoir 42 and drive the drug therefrom.

Pump 41 is connected via a length of non-kinking flexible tubing 46 to the inlet of device 10, such that when pumping begins the internal chamber 12 in device 10 expands and contracts as described above in relation to FIGS. 1–5, resulting in the generation of fluid pulses through a delivery tube 47. Delivery tube 47 is provided with a lube adapter 48 for connection to an intravenous injection set.

A restrictor (not visible) is provided between pump 41 and device 10. The restrictor comprises a narrow section of tubing through which the drug passes, the diameter of the restrictor controlling the rate at which the drug enters the device 10. This in turn determines the period of the cycle of pulse generation (as can be appreciated with reference to the description of FIGS. 1–5). Thus, the rate of pulse generation can be controlled by the choice of a suitable restrictor. Because neither device 10 nor pump 41 relies on batteries or any other exhaustible energy supply, the rate of pulse generation can be slowed down to any desired extent, by slowing the rate at which drug is delivered from pump 41 to device 10 (via the restrictor).

Figure 7:
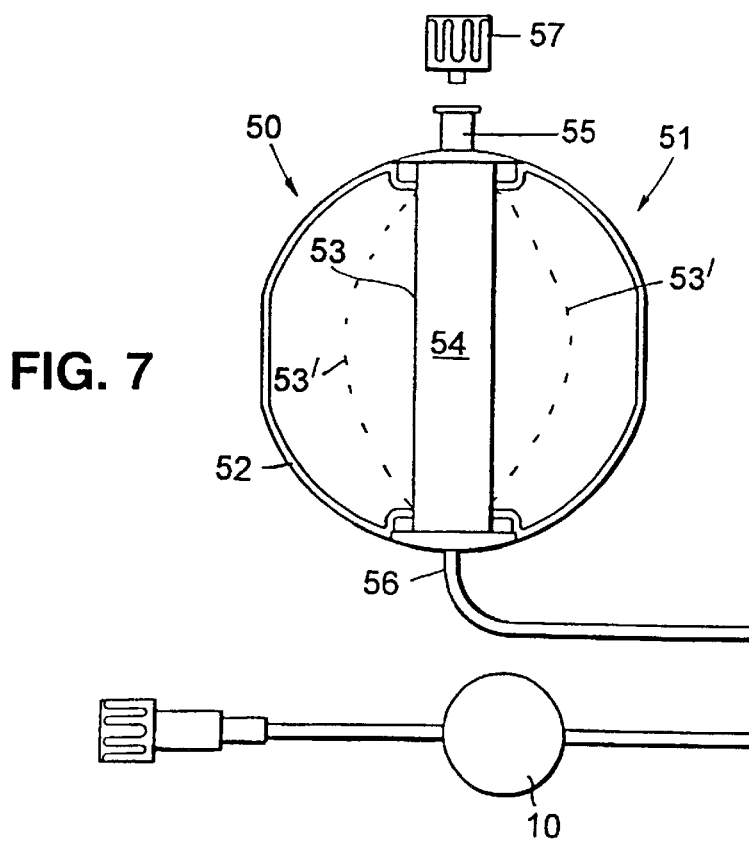
FIG. 7 shows a system according to the invention incorporating an elastomeric pump.

In FIG. 7 there is indicated, generally at 50, a further system according to the invention comprising a device 10 as previously described and an elastomeric pump, indicated generally at 51 in sectional elevation.

The only difference between system 51 (FIG. 7) and system 41 (FIG. 6) is that the pumps used are different The skilled person will also be familiar with the operation of the elastomeric pump 51 which will now be described for the sake of completeness.

The pump 51 consists essentially of a housing 52 in which a generally cylindrical elastomeric ("balloon") membrane 53 is mounted. Membrane 53 defines a reservoir 54 which communicates at one end thereof with a medication fill port 55 and at the other end thereof with a delivery outlet 56. Fill port 55 is provided with a removable sealing cap 57 and is used for filling the reservoir 54. When filled, reservoir 54 is expanded to the shape illustrated in dotted outline , and the energy for delivery is stored in as elastic energy in the expanded membrane 53'. Delivery occurs through delivery outlet 56 and the drug is supplied at a constant rate to device 10 as described in relation to the system of FIG. 6.

Figure 8:
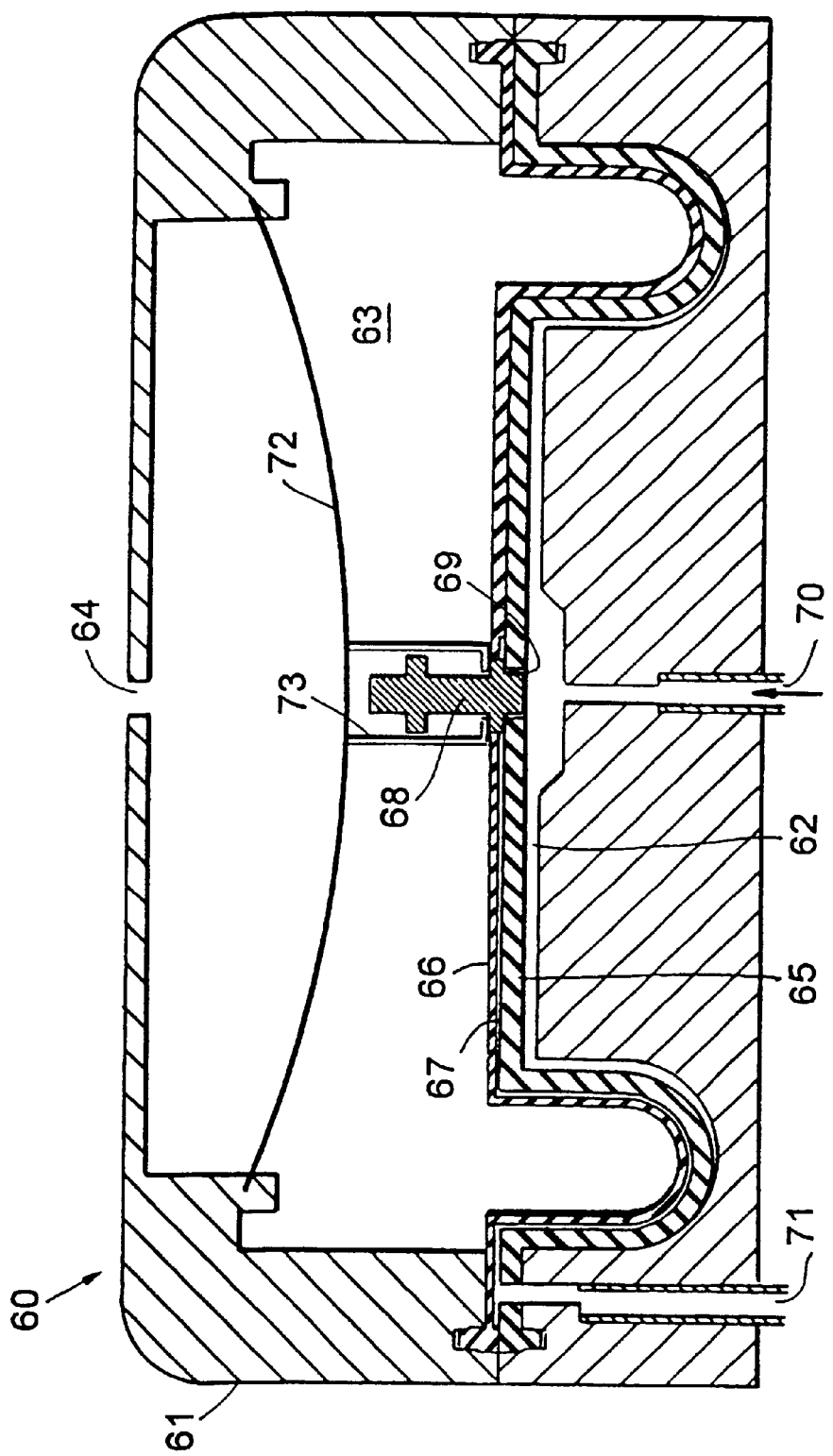
FIG. 8 is a sectional elevation of a second device according to the invention.

In FIG. 8 there is indicated, generally at 60, a second device according to the invention comprising a cylindrical housing 61 containing a medicament chamber 62 (shown in a contracted state) and an atmospheric chamber 63 which is open to the atmosphere via an orifice 64 so as to allow the medicament chamber to expand and contract.

Medicament chamber 62 is partially bounded by a flexible resilient elastomeric lower diaphragm 65, and atmospheric chamber 63 is partially bounded by a flexible resilient elastomeric upper diaphragm 66. Lower diaphragm 65 and upper diaphragm 66 are adjacent to but separated from one another so that a gap 67 is provided between the diaphragms 65, 66. The central portion of upper diaphragm 66 is provided with an integral blocking member 68, however, which makes a tight seal with an aperture 69 in lower diaphragm 65, thereby preventing communication between medicament chamber 62 and gap 67 when the device is in the configuration shown in FIG. 8.

Medicament chamber 62 is provided with an inlet 70 which can be connected to a continuous flow drug source, as described above in relation to device 10, and gap 67 communicates with an outlet 71. Furthermore, atmospheric chamber 63 contains a spring 72 consisting of a thin convex circular metal disc which can be flipped between concave and convex configurations and from which a member 73 depends. The function of these elements will be explained below in relation to the operation of the device.

Figure 9:
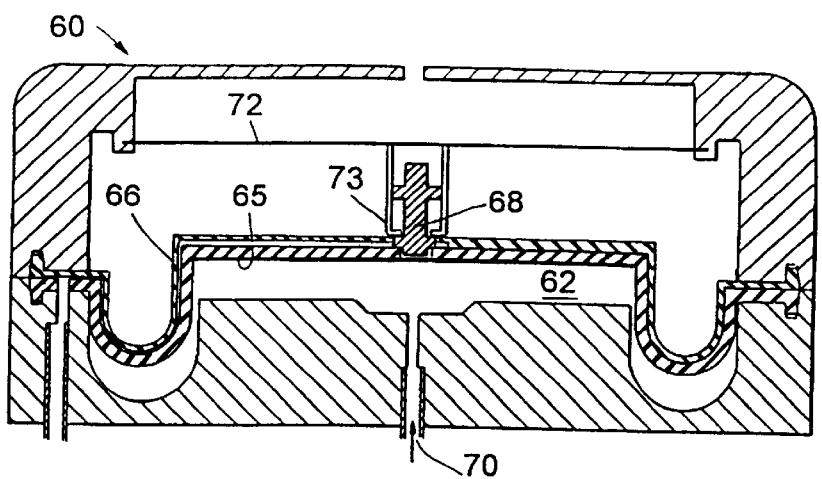
FIGS. 9–11 show the device of FIG. 8 as it progresses through a pumping cycle.

Referring additionally to FIG. 9, the operation of device 60 is as follows. In use, device 60 is connected to a continuous flow drug source via inlet 70. This causes medicament chamber 62 to begin to fill with the drug under pressure from the incoming medicament. The medicament chamber 62 expands as lower and upper diaphragms 65, 66 are pushed upwards by the pressure in medicament chamber 62. This upward movement also causes spring 72 to be deformed upwards because blocking member 68 acts on member 73 and thus also on spring 72. The opposing force from spring 72 via member 73 onto blocking member 68 prevents blocking member 68 from moving out of sealing engagement with lower diaphragm 65.

Figure 10:
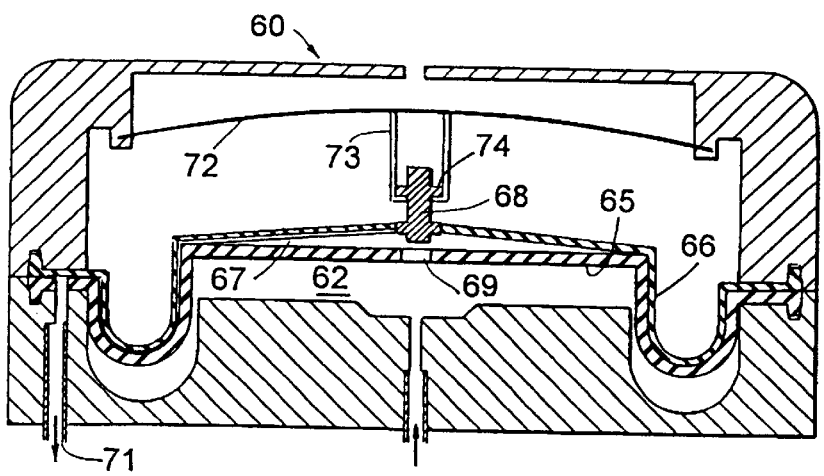

When spring 72 is pushed past the point shown in FIG. 9 it flips up into the position shown in FIG. 10, causing member 73 to engage a widened section 74 of blocking member 68 thereby moving blocking member 68 upwards out of sealing engagement with lower diaphragm 65. This opens communication between medicament chamber 62 and gap 67 via aperture 69.

Figure 11:
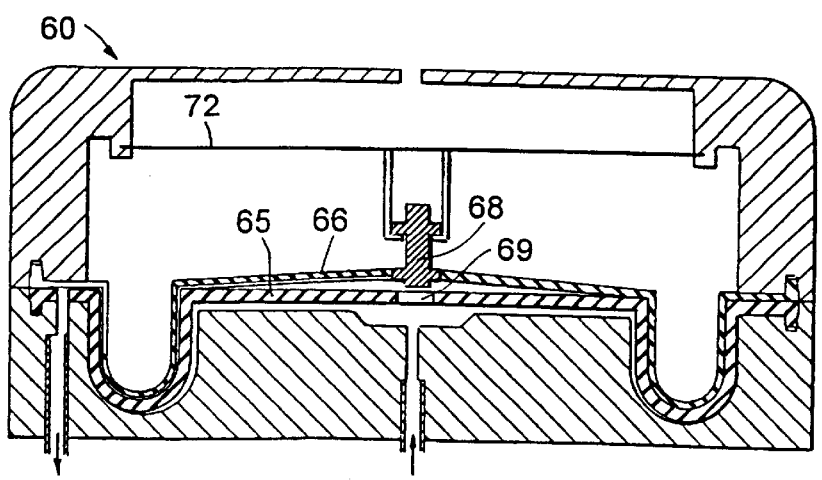

When aperture 69 is thus unsealed, the medicament which fills medicament chamber 62 flows through gap 67 and out of device 60 through outlet 71 as it is under pressure within medicament chamber 62. Thus, aperture 69 serves as an outlet from medicament chamber 62 allowing the medicament to exit from the device through gap 67 and outlet 71. The resilience of lower diaphragm 65, which is biased to return to the position shown in FIG. 8, together with the elasticity of upper diaphragm 66, which is relaxed in FIGS. 8 and 9 but stretched in FIG. 10, assists in emptying medicament chamber 62. As shown in FIG. 11, the downward movement of lower and upper diaphragms 65, 66 causes spring 72 to move back towards the starting position. The fact that blocking member 68 is pulling spring 72 downwards means that aperture 69 remains open in the stage of the pumping cycle between FIGS. 10 and 11, allowing medicament chamber 62 to empty fully.

When the spring 72 moves past the position shown in FIG. 11 it snaps downwards, thereby pushing blocking member 68 downwards into sealing engagement with aperture 69 and returning device 60 to the starting configuration shown in FIG. 8, at which point the cycle begins again. The device of FIGS. 8–11 thus operates with a similar cycle to the device of FIGS. 1–4, but it will be noted that in the device of FIGS. 8–11, the spring and associated mechanism are removed from the path of the medicament, which may be advantageous in ensuring sterility of the medicament or in ensuring correct operation of the device (if a particularly unstable or viscous medicament were to be pumped, for example). Thus, if the material used for the spring is a metal which is unsuitable for prolonged immersion in the medicament in question, the device of FIGS. 8–11 can be used, as in this embodiment the medicament only comes into contact with the elastomeric diaphragm materials and the interior of the housing, the remainder of the mechanism being located in the atmospheric chamber.

What is claimed is:

1. A device for generating a pulsatile drug flow, comprising:

a housing containing an expandable/contractible chamber having an inlet and an outlet, a valve, associated with the outlet, the valve being actuated by a bistable actuating member lied to the displacement member, the bistable actuating member acts on the valve to open and close the valve as tie bistable actuating member moves between its bistable configurations, and the valve being shaped to allow the bistable actuating member to undergo an initial deformation or movement without actuating the valve such that an actuation of the valve only occurs when the actuating member undergoes the full transition between its bistable configurations;

a displacement member that through its displacement controls the expansion and contraction of the chamber and the actuation of the valve; and a resilient member for biasing the chamber to its contracted state such that when the inlet is connected to a pressurised fluid drug supply the chamber is expanded by the drug, the expansion of the chamber actuating the valve to open, thereby allowing a release of drug from the chamber and enabling the contraction of the chamber under the influence of the resilient member, this contraction in turn actuating the valve to close thereby allowing the chamber to refill.

2. A device according to claim 1, wherein said component of the valve is in the form of a longitudinally extending element having a section of lesser thickness intermediate two sections of greater thickness, and the bistable actuating member is provided with an aperture which moves freely with respect to the section of lesser thickness but which engages the sections of greater thickness.

3. A device according to claim 1 wherein the resilient member acts on a displaceble member which at least partially bounds the chamber such the expansion end contraction of the chamber occurs by the displacement of the displaceable member, and the outlet is formed by an aperture in the displaceable member, the aperture forming a seat for tho valve, and where the displaceable member is selected from a movable wall section, a diaphragm, a membrane and a bellows.

4. A device according to claim 3, wherein the valve comprises a blocking member which is adapted to move into and out of sealing engagement with the seat, thereby opening and closing said outlet.

5. A device according to claim 4, wherein the blocking member is carried on a second displaceable member and the aperture communicates with the exterior of the device via a gap between the displaceable members.

6. A device according to claim 5, wherein the second displaceable member is elastic and is biased to a position in which the blocking member is in sealing engagement with the aperture.

7. A device according to claim 1 which is adapted to be connected to and to receive a supply of fluid drug from a continuous flow drug pump.

\* \* \* \* \*